United States Patent
Aubert et al.

(10) Patent No.: US 10,449,140 B2
(45) Date of Patent: *Oct. 22, 2019

(54) COMPOSITION BASED ON STYLING POWDER AND/OR SEBUM-ABSORBING POWDER AND AN ALUMINIUM SALT

(71) Applicant: L'OREAL, Paris (FR)

(72) Inventors: Lionel Aubert, Asnieres sur Oise (FR); Nathalie Beau, Eragny-sur-Oise (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/523,242

(22) PCT Filed: Oct. 29, 2015

(86) PCT No.: PCT/EP2015/075062
§ 371 (c)(1),
(2) Date: Apr. 28, 2017

(87) PCT Pub. No.: WO2016/066730
PCT Pub. Date: May 6, 2016

(65) Prior Publication Data
US 2017/0312212 A1    Nov. 2, 2017

(30) Foreign Application Priority Data

Oct. 29, 2014    (FR) ..................................... 14 60405

(51) Int. Cl.
| | | |
|---|---|---|
| *A61K 8/73* | (2006.01) | |
| *A61K 8/26* | (2006.01) | |
| *A61Q 5/02* | (2006.01) | |
| *A61K 8/02* | (2006.01) | |
| *A61K 8/19* | (2006.01) | |
| *A61K 8/49* | (2006.01) | |
| *A61K 8/04* | (2006.01) | |
| *A61K 8/25* | (2006.01) | |
| *A61K 8/31* | (2006.01) | |
| *A61K 8/37* | (2006.01) | |
| *A61K 8/27* | (2006.01) | |

(52) U.S. Cl.
CPC .............. *A61K 8/732* (2013.01); *A61K 8/022* (2013.01); *A61K 8/046* (2013.01); *A61K 8/19* (2013.01); *A61K 8/25* (2013.01); *A61K 8/26* (2013.01); *A61K 8/31* (2013.01); *A61K 8/37* (2013.01); *A61K 8/4913* (2013.01); *A61Q 5/02* (2013.01); *A61K 8/27* (2013.01); *A61K 2800/31* (2013.01)

(58) Field of Classification Search
None
See application file for complete search history.

(56) References Cited

U.S. PATENT DOCUMENTS

| | | |
|---|---|---|
| 2,047,398 A | 7/1936 | Voss et al. |
| 2,102,113 A | 12/1937 | Djordjevitch |
| 2,723,248 A | 11/1955 | Wright |
| 3,161,460 A | 12/1964 | Huber |
| 3,504,862 A | 4/1970 | Lowry |
| 3,579,629 A | 5/1971 | Pasero et al. |
| 3,589,978 A | 6/1971 | Kamal et al. |
| 3,628,733 A | 12/1971 | Kahn |
| 3,716,633 A | 2/1973 | Viout et al. |
| 3,767,125 A | 10/1973 | Gehres et al. |
| 3,792,068 A | 2/1974 | Luedders et al. |
| 3,810,977 A | 5/1974 | Levine et al. |
| 3,836,537 A | 9/1974 | Boerwinkle et al. |
| 3,910,862 A | 10/1975 | Barabas et al. |
| 3,925,542 A | 12/1975 | Viout et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,031,307 A | 6/1977 | DeMartino et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,165,367 A | 8/1979 | Chakrabarti |
| 4,223,009 A | 9/1980 | Chakrabarti |

(Continued)

FOREIGN PATENT DOCUMENTS

| | | |
|---|---|---|
| DE | 2330956 A1 | 1/1974 |
| DE | 10-2008035013 A1 | 1/2010 |

(Continued)

OTHER PUBLICATIONS

Mintel. "72h Anti-Perspirant Deodorant." XP007923192. Jan. 2014, 4 printed pages.*
Mintel. "Dry Shampoo." Rene Furterer. XP007923191. Jan. 2014, 4 printed pages.*
Foot Deodorant Spray. "Retycol." XP007923193. Oct. 2013, 2 printed pages.*
International Search Report for PCT/FR2015/051896, dated Oct. 19, 2015.
International Search Report for PCT/EP2015/075061, dated Jan. 20, 2016.
International Search Report for PCT/EP2015/075062, dated Jan. 26, 2016.

(Continued)

*Primary Examiner* — Isaac Shomer
(74) *Attorney, Agent, or Firm* — The Marbury Law Group, PLLC

(57) ABSTRACT

A subject of the present invention is a composition comprising: a) at least one sebum-absorbing powder with a sebum uptake of greater than or equal to 35 ml/100 g, and/or at least one styling powder; b) at least one aluminum salt other than the sebum-absorbing powders with a sebum uptake of greater than or equal to 35 ml/100 g, and/or than the styling powders; c) optionally a propellant. A subject of the present invention is also to a process for the thy-washing and cosmetic treatment of keratin materials, comprising a step of applying the composition to the hair.

23 Claims, No Drawings

(56) References Cited

U.S. PATENT DOCUMENTS

| | | | |
|---|---|---|---|
| 4,282,203 A | 8/1981 | Jacquet et al. | |
| 4,389,752 A | 6/1983 | Briner et al. | |
| 4,401,271 A | 8/1983 | Hansen | |
| 4,450,151 A | 5/1984 | Shinozawa | |
| 4,557,916 A | 12/1985 | Withiam | |
| 4,605,553 A * | 8/1986 | Passalacqua | A61K 8/25 424/59 |
| 4,693,925 A | 9/1987 | Cheung et al. | |
| 4,728,571 A | 3/1988 | Clemens et al. | |
| 4,822,596 A | 4/1989 | Callingham et al. | |
| 4,871,529 A | 10/1989 | Sramek | |
| 4,874,554 A | 10/1989 | Lange et al. | |
| 4,957,732 A | 9/1990 | Grollier et al. | |
| 4,972,037 A | 11/1990 | Garbe et al. | |
| 4,983,377 A | 1/1991 | Murphy et al. | |
| 5,297,739 A | 3/1994 | Allen | |
| 5,300,284 A | 4/1994 | Wiechers et al. | |
| 5,508,259 A | 4/1996 | Holzner et al. | |
| 5,538,717 A | 7/1996 | La Poterie | |
| 5,614,173 A | 3/1997 | Ulmer et al. | |
| 5,643,557 A | 7/1997 | Eteve et al. | |
| 5,879,669 A | 3/1999 | Clausen et al. | |
| 6,106,813 A | 8/2000 | Mondet et al. | |
| 6,166,093 A | 12/2000 | Mougin et al. | |
| 6,210,689 B1 | 4/2001 | Martino et al. | |
| 6,245,324 B1 * | 6/2001 | Hough | A61K 8/25 424/400 |
| 6,319,959 B1 | 11/2001 | Mougin et al. | |
| 6,350,434 B1 | 2/2002 | Bhatt et al. | |
| 6,372,876 B1 | 4/2002 | Kim et al. | |
| 6,395,265 B1 | 5/2002 | Mougin et al. | |
| 6,592,854 B1 | 7/2003 | Dupuis | |
| 6,751,886 B2 | 6/2004 | Chang et al. | |
| 7,063,834 B2 | 6/2006 | Mougin et al. | |
| 7,585,824 B2 | 9/2009 | Popplewell et al. | |
| 2002/0031478 A1 | 3/2002 | Keller et al. | |
| 2002/0150546 A1 | 10/2002 | Mougin et al. | |
| 2003/0163878 A1 | 9/2003 | Pruche | |
| 2003/0185777 A1 * | 10/2003 | Banowski | A61K 8/26 424/66 |
| 2003/0191271 A1 | 10/2003 | Mondet et al. | |
| 2004/0047812 A1 | 3/2004 | Pataut et al. | |
| 2004/0170575 A1 | 9/2004 | Belli et al. | |
| 2004/0175404 A1 | 9/2004 | Shefer et al. | |
| 2005/0163737 A1 | 7/2005 | Lemoine et al. | |
| 2005/0220723 A1 | 10/2005 | Benabdillah et al. | |
| 2008/0019928 A1 | 1/2008 | Franzke et al. | |
| 2008/0172807 A1 | 7/2008 | Brun | |
| 2008/0274071 A1 | 11/2008 | Kaplan et al. | |
| 2009/0061004 A1 | 3/2009 | Birkel et al. | |
| 2010/0040572 A1 | 2/2010 | Mougin | |
| 2012/0097180 A1 | 4/2012 | Harris et al. | |
| 2012/0171264 A1 | 7/2012 | Bernet et al. | |
| 2012/0282190 A1 | 11/2012 | Hammer | |
| 2013/0289080 A1 | 10/2013 | Masse et al. | |
| 2013/0340786 A1 | 12/2013 | Rodrigues et al. | |
| 2014/0030196 A1 * | 1/2014 | Russell | A61K 8/732 424/59 |
| 2014/0079747 A1 | 3/2014 | Dihora et al. | |
| 2015/0041559 A1 | 2/2015 | Albisetti | |
| 2015/0104397 A1 | 4/2015 | Small et al. | |
| 2015/0139917 A1 | 5/2015 | Gawtrey et al. | |
| 2016/0106634 A1 | 4/2016 | Gawtrey et al. | |
| 2018/0016087 A1 | 1/2018 | Smail et al. | |

FOREIGN PATENT DOCUMENTS

| | | |
|---|---|---|
| EP | 0080976 A1 | 6/1983 |
| EP | 0095238 A2 | 11/1983 |
| EP | 0186507 A2 | 7/1986 |
| EP | 0342834 A2 | 11/1989 |
| EP | 0412704 A2 | 2/1991 |
| EP | 0412707 A1 | 2/1991 |
| EP | 0530974 A1 | 3/1993 |
| EP | 0582152 A2 | 2/1994 |
| EP | 0619111 A1 | 10/1994 |
| EP | 0637600 A1 | 2/1995 |
| EP | 0648485 A1 | 4/1995 |
| EP | 0751162 A1 | 1/1997 |
| EP | 0 974 332 A1 | 1/2000 |
| EP | 1026220 A1 | 8/2000 |
| EP | 1407754 A1 | 4/2004 |
| EP | 2444160 A1 | 4/2012 |
| EP | 2777770 A1 | 9/2014 |
| FR | 1400366 A | 5/1965 |
| FR | 1578989 A | 8/1969 |
| FR | 1580545 A | 9/1969 |
| FR | 1600138 A | 7/1970 |
| FR | 2077143 A5 | 10/1971 |
| FR | 2198719 A1 | 4/1974 |
| FR | 2265781 A1 | 10/1975 |
| FR | 2265782 A1 | 10/1975 |
| FR | 2350384 A1 | 12/1977 |
| FR | 2357241 A2 | 2/1978 |
| FR | 2393573 A1 | 1/1979 |
| FR | 2434194 A1 | 3/1980 |
| FR | 2439798 A1 | 5/1980 |
| FR | 2589476 A1 | 5/1987 |
| FR | 2715841 A1 | 8/1995 |
| FR | 2743297 A1 | 7/1997 |
| FR | 2814943 A1 | 4/2002 |
| FR | 2924341 A1 | 6/2009 |
| FR | 2980125 A1 | 3/2013 |
| FR | 2985201 A1 | 7/2013 |
| FR | 2985202 A1 | 7/2013 |
| FR | 2990131 A1 | 11/2013 |
| FR | 2990133 A1 | 11/2013 |
| FR | 3004929 A1 | 10/2014 |
| GB | 839805 A | 6/1960 |
| GB | 922457 A | 4/1963 |
| GB | 1021400 A | 3/1966 |
| GB | 1218222 A | 1/1971 |
| GB | 1235908 A | 6/1971 |
| GB | 1331819 A | 9/1973 |
| GB | 1408388 A | 10/1975 |
| GB | 1572626 A | 7/1980 |
| JP | 2011-213619 A | 10/2011 |
| LU | 75370 A1 | 2/1978 |
| LU | 75371 A1 | 2/1978 |
| WO | 93/23009 A1 | 11/1993 |
| WO | 94/03510 A1 | 2/1994 |
| WO | 95/00578 A1 | 1/1995 |
| WO | 98/43599 A1 | 10/1998 |
| WO | 02/078653 A1 | 10/2002 |
| WO | 02/096379 A1 | 12/2002 |
| WO | 03/049711 A2 | 6/2003 |
| WO | 2004/043608 A1 | 5/2004 |
| WO | 2011/019539 A2 | 2/2011 |
| WO | 2011/056625 A1 | 5/2011 |
| WO | 2012/035053 A1 | 3/2012 |
| WO | 2012/080255 A2 | 6/2012 |
| WO | 2013/064918 A1 | 5/2013 |
| WO | 2013/167530 A2 | 11/2013 |
| WO | 2013/167536 A2 | 11/2013 |
| WO | 2014/177646 A2 | 11/2014 |
| WO | 2014/177647 A1 | 11/2014 |
| WO | 2014/177649 A1 | 11/2014 |
| WO | 2016/001190 A1 | 1/2016 |
| WO | 2016/005703 A1 | 1/2016 |
| WO | 2016/066729 A1 | 5/2016 |
| WO | 2016/110575 A1 | 7/2016 |
| WO | 2016/110578 A1 | 7/2016 |
| WO | 2016/110579 A1 | 7/2016 |

OTHER PUBLICATIONS

Brunauer et al., "Adsorption of Gases in Multimolecular Layers," Journal of the American Chemical Society, vol. 60, Feb. 1938, pp. 309-319.

Mintel: Apr. 2010, "Refresh Dry Shampoo".

Mintel: "Code 10 Hair Styling Cream," XP007923186 (Sep. 2001).

(56) References Cited

OTHER PUBLICATIONS

Mintel: "One More Day Dry Shampoo," XP007923187 (Aug. 2013).
Mintel: "Foot Deodorant Spray," XP007923193 (Oct. 2013).
Mintel: "72h Anti-Perspirant Deodorant," XP007923192 (Jan. 2014).
Mintel: "Dry Shampoo," XP007923191 (Jan. 2014).
Non-Final Office Action for copending U.S. Appl. No. 14/787,983, dated May 11, 2018.
International Search Report for PCT/EP2013/0509382, dated Jun. 20, 2014.
International Search Report for PCT/EP2013/059393, dated Jun. 20, 2014.
Database WPI Week 201172, Thomas Scientific, London, GB, AN 2011-N36295, XP002690571, dated Jan. 25, 2013.
Mintel: "Brown Hair Powder Shampoo," XP002690821, Jun. 2011.
Oscar Blandi, http://www.skinstore.com/p-6885-oscar-blandi-pronto-dry-shampoo-spray.aspx. published Jun. 3, 2011.
Non-Final Office Action for copending U.S. Appl. No. 14/399,753, dated Sep. 8, 2015.
Final Office Action for copending U.S. Appl. No. 14/399,753, dated Mar. 30, 2016.
Non-Final Office Action for copending U.S. Appl. No. 14/399,764, dated Dec. 17, 2015.
International Search Report for PCT/EP2014/058896, dated Sep. 23, 2014.
International Search Report and Written Opinion for PCT/EP2014/058892, dated Oct. 29, 2014.
International Search Report for PCT/EP2014/058894, dated Sep. 29, 2014.
Final Office Action for copending U.S. Appl. No. 14/399,764, dated Aug. 5, 2016.
Non-Final Office Action for copending U.S. Appl. No. 14/888,002, dated Sep. 9, 2016.
Non-Final Office Action for copending U.S. Appl. No. 14/787,983, dated Sep. 15, 2016.
Final Office Action for copending U.S. Appl. No. 14/399,753, dated Sep. 30, 2016.
Non-Final Office Action for copending U.S. Appl. No. 14/888,013, dated Apr. 13, 2017.
Non-Final Office Action for copending U.S. Appl. No. 14/399,764, dated Mar. 8, 2017.
Final Office Action for copending U.S. Appl. No. 14/787,983, dated May 30, 2017.
Non-Final Office Action for copending U.S. Appl. No. 15/523,804, dated Mar. 5, 2018.
Bezard et al., "Triglycerides of Coconut Oil," Journal of American Oil Society, 48, 3, Mar. 1971, pp. 134-139.
Final Office Action for copending U.S. Appl. No. 14/888,013, dated Aug. 15, 2007.
Final Office Action for copending U.S. Appl. No. 14/888,002, dated Sep. 21, 2017.
Final Office Action for copending U.S. Appl. No. 14/399,764, dated Aug. 16, 2017.
Non-Final Office Action for copending U.S. Appl. No. 14/399,753, dated Oct. 4, 2017.
International Search Report for counterpart Application PCT/EP2011/072617, dated Jul. 5, 2012.
Todd, Charles, et al., "Volatile Silicone Fluids for Cosmetic Formulations," Cosmetics and Toiletries, vol. 91, Jan. 1976, pp. 29-32.
International Search Report for counterpart Application PCT/EP2016/050295, dated Mar. 23, 2016.
International Search Report for counterpart Application PCT/EP2016/050299, dated Mar. 23, 2016.
International Search Report for counterpart Application PCT/EP2016/050300, dated Mar. 16, 2016.
Non-Final Office Action for copending U.S. Appl. No. 15/541,738, dated May 17, 2018.
Non-Final Office Action for copending U.S. Appl. No. 13/993,413, dated May 19, 2015.
Final Office Action for copending U.S. Appl. No. 13/993,413, dated Dec. 30, 2015.
Non-Final Office Action for copending U.S. Appl. No. 13/993,413, dated Nov. 8, 2017.
Final Office Action for copending U.S. Appl. No. 13/993,413, dated Jul. 5, 2018.
Oxford Dictionary, Half-Ester, http://www.oxfordreference.com/view/10.1093/acref/9780198529170.001.0001/acref-9780198529170-e-8589, retrieved online on Oct. 19, 2017 (Year:2017).
Final Office Action for copending U.S. Appl. No. 13/993,413, dated Nov. 14, 2016.
Final Office Action for copending U.S. Appl. No. 15/324,804, dated Nov. 30, 2018.
Non-Final Office Action for copending U.S. Appl. No. 14/399,764, dated Dec. 5, 2018.
Final Office Action for copending U.S. Appl. No. 14/787,983, dated Dec. 27, 2018.
Final Office Action for copending U.S. Appl. No. 15/523,232, dated Jan. 25, 2019.
Non-Final Office Action for copending U.S. Appl. No. 15/541,738, dated Feb. 5, 2019.
Final Office Action for co-pending U.S. Appl. No. 14/781,983, dated Dec. 27, 2018.
Non-Final Office Action for co-pending U.S. Appl. No. 15/541,741, dated Feb. 27, 2019.
International Search Report for counterpart Application No. PCT/EP2015/064780, dated Sep. 14, 2015.
Porter, M.R., "Handbook of Surfactants," published by Blackie & Son (Glasgow and London), 1991, pp. 116-178.
Mintel: "Styling Mousse," XP002736036, Nov. 2008.
Non-Final Office Action for co-pending U.S. Appl. No. 14/888,013, dated Mar. 14, 2019.
Mintel: "Clean Freak Refreshing Dry Shampoo," XP007923188, Demert Brands, Mar. 2014.
Final Office Action for co-pending U.S. Appl. No. 14/399,764, dated Jun. 7, 2019.
Non-Final Office Action for co-pending U.S. Appl. No. 14/787,983, dated Jun. 26, 2019.
Final Office Action for co-pending U.S. Appl. No. 15/541,741, dated Jul. 11, 2019.

\* cited by examiner

COMPOSITION BASED ON STYLING POWDER AND/OR SEBUM-ABSORBING POWDER AND AN ALUMINIUM SALT

CROSS REFERENCE TO RELATED APPLICATIONS

This is a national stage application of PCT/EP2015/075062, filed internationally on Oct. 29, 2015, which claims priority to French Application No. 1460405, filed on Oct. 29, 2014, both of which are incorporated by reference herein in their entireties.

In the field of washing keratin materials, dry shampoos have existed for many years, either in a powdery form or in aerosol form. They enable excess sebum to be removed quickly without wetting the head of hair. They act by taking up sebum by absorption by means of powders chosen for their sebum-absorbing qualities.

The powders used may be of mineral, organic or synthetic origin and may be wheat, rice and maize starch derivatives.

In practice, the proposed dry shampoos are not entirely satisfactory. Their styling properties, such as giving the head of hair volume and lifting the roots, are generally very limited. Moreover, they do not allow excess sebum present on the scalp, and the discomfort caused such as irritation or odours, to be eliminated. Moreover, stability of shampoos containing powders is difficult to achieve.

There is thus a need to develop a novel dry shampoo composition which both offers optimum cleansing activity and gives the head of hair volume, with improved stability.

The Applicant has found, surprisingly and advantageously, that the use of at least one sebum-absorbing powder and/or of a styling powder in combination with at least one aluminium salt other than the absorbing and/or styling powders makes it possible to offer the cleansing properties expected of a dry shampoo and also styling properties such as giving the head of hair volume and body. The compositions according to the invention provide a soothing and/or deodorizing effect to the scalp.

Moreover, the composition of the invention has improved stability.

When the composition is in aerosol form, the composition may be satisfactorily distributed.

Moreover, the composition of the invention leaves less white residue than the products conventionally used.

Finally, the composition of the invention is well tolerated by the scalp.

The subject of the invention is thus a composition comprising:
a) at least one sebum-absorbing powder with a sebum uptake of greater than or equal to 35 ml/100 g, and/or at least one styling powder;
b) at least one aluminium salt other than the sebum-absorbing powders with a sebum uptake of greater than or equal to 35 ml/100 g, and/or than the styling powders;
c) optionally a propellant.

The composition is preferably anhydrous. For the purposes of the present invention, the term "anhydrous composition" means a composition having a water content of less than 5% by weight, preferably less than 2% by weight, and/or a composition which does not contain any added water, that is to say that the water which may be present in the composition according to the invention is more particularly bound water, such as the water of crystallization of salts, or traces of water absorbed by the starting materials used in the production of the compositions according to the invention.

According to one embodiment, the composition comprises at least one sebum-absorbing powder with a sebum uptake of greater than or equal to 35 ml/100 g, and at least one styling powder.

According to another embodiment, the composition of the invention comprises at least one propellant.

According to the invention, the composition may comprise one or more sebum-absorbing powders with a sebum uptake of greater than or equal to 35 ml/100 g, For the purposes of the present invention, the term "sebum-absorbing powder" means a powder that is capable of absorbing and/or adsorbing sebum, which has a sebum uptake of greater than or equal to 35 ml/100 g.

The sebum uptake corresponds to the amount of sebum absorbed and/or adsorbed by the powder. It is expressed in ml of sebum per 100 g of powder and is measured using the method for determining the oil uptake of a powder described in standard NF T 30-022.

The oil uptake of a powder corresponds to the amount of sebum absorbed onto the available surface of the powder by measuring the "wet point" as indicated below.

The measuring method is as follows: an amount m (in grams) of between 0.5 and 5 grams of powder is placed on a glass plate, the amount depending on the density of the powder, followed by dropwise addition of artificial sebum having the following composition:

| | |
|---|---|
| Triolein | 29% by weight |
| Oleic acid | 28.5% by weight |
| Oleyl oleate | 18.5% by weight |
| Squalene | 14% by weight |
| Cholesterol | 7% by weight |
| Cholesteryl palmitate | 3% by weight |

After addition of 4 to 5 drops of artificial sebum, the artificial sebum is incorporated into the powder using a spatula, and addition of the artificial sebum is continued until conglomerates of artificial sebum and powder have formed. At this point, the artificial sebum is added one drop at a time and the mixture is then triturated with the spatula.

The addition of artificial sebum is stopped when a firm, smooth paste is obtained. This paste must be able to be spread on the glass plate without cracking or forming lumps. The volume Vs, in ml, of artificial sebum used is then noted.

The sebum uptake corresponds to the ratio Vs/m.

The sebum-absorbing powder(s) used in the composition according to the invention have a sebum uptake preferably ranging from 35 to 1000 ml/100 g and even better still from 35 to 800 ml/100 g.

Advantageously, the sebum-absorbing particle may have a BET specific surface area of greater than or equal to 150 $m^2/g$, preferably greater than or equal to 300 $m^2/g$, better still greater than 500 $m^2/g$ and preferentially greater than 600 $m^2/g$, and especially less than 1500 $m^2/g$.

The BET specific surface area is determined according to the BET (Brunauer-Emmett-Teller) method described in the Journal of the American Chemical Society, vol. 60, page 309, February 1938, which corresponds to international standard ISO 5794/1 (appendix D). The BET specific surface area corresponds to the total specific surface area (thus including micropores) of the particle and especially of the powder.

The sebum-absorbing powder may be a mineral powder or an organic powder.

More precisely, the sebum-absorbing powder may be chosen from:

starches,
calcium silicates,
perlites,
zeolites,
polylactic acids,
silicas,
polyamide (Nylon®) powders,
powders of acrylic polymers, in particular of polymethyl methacrylate, of poly(methyl methacrylate/ethylene glycol dimethacrylate), of poly(allyl methacrylate/ethylene glycol dimethacrylate) or of ethylene glycol dimethacrylate/lauryl methacrylate copolymer;
silicone elastomer powders, obtained especially by polymerization of organopolysiloxane containing at least two hydrogen atoms each bonded to a silicon atom and of an organopolysiloxane comprising at least two ethylenically unsaturated groups (especially two vinyl groups) in the presence of a platinum catalyst; and
mixtures thereof.

The sebum-absorbing powder may be a powder coated with a hydrophobic treatment agent.

The hydrophobic treatment agent can be chosen from fatty acids, such as stearic acid; metal soaps, such as aluminium dimyristate or the aluminium salt of hydrogenated tallow glutamate; amino acids; N-acylamino acids or their salts; lecithin, isopropyl-triisostearyl titanate, and mixtures thereof.

The N-acylamino acids can comprise an acyl group containing from 8 to 22 carbon atoms, for instance a 2-ethylhexanoyl, caproyl, lauroyl, myristoyl, palmitoyl, stearoyl or cocoyl group. The salts of these compounds can be the aluminium, magnesium, calcium, zirconium, zinc, sodium or potassium salts. The amino acid can, for example, be lysine, glutamic acid or alanine.

The term "alkyl" mentioned in the compounds cited above denotes in particular an alkyl group containing from 1 to 30 carbon atoms and preferably containing from 5 to 16 carbon atoms.

The starches which can be used in the present invention are, for example, maize starch, potato starch, tapioca starch, rice starch, wheat starch and cassava starch.

The starches may or may not be modified.

A modified starch is a starch which has been modified by processes known to a person skilled in the art, such as, for example, esterification, etherification, oxidation, acid hydrolysis, crosslinking or enzymatic conversion.

Non-limiting examples of modified starch comprise aluminium starch octenylsuccinate, sodium starch octenylsuccinate, calcium starch octenylsuccinate, distarch phosphate, hydroxyethyl starch phosphate, hydroxypropyl starch phosphate, sodium carboxymethyl starch and sodium starch glycolate.

In one particular embodiment, the starch is a starch octenylsuccinate, in particular an aluminium starch octenylsuccinate, the starch being from maize, wheat or rice. Mention may be made especially of the product sold by Akzo Nobel under the name Dry Flo Plus.

Preferably, the calcium silicates used as sebum-absorbing powder exhibit a sebum uptake of greater than 200 ml/100 g, better still between 400 ml/100 g and 600 ml/100 g and more preferentially of approximately 475 ml/100 g.

The specific surface area (BET) preferably ranges from approximately 150 m$^2$/g to 600 m$^2$/g, better still from 300 m$^2$/g to 600 m$^2$/g and even more preferentially from 310 m$^2$/g to 350 m$^2$/g.

The size of the silicate particles is preferably less than 20 micrometers.

These calcium silicates are generally prepared by reaction of reactive silica with an alkaline-earth metal reagent, preferably an alkaline-earth metal oxide or hydroxide, and a source of aluminium such as sodium aluminate or alumina. As the final properties of the silicate depend on the reactivity of the silica, the preferred source of silica is the reaction product of a soluble silicate, such as sodium silicate, and of a mineral acid, such as sulfuric acid. Suitable amorphous synthetic alkaline-earth metal silicates are manufactured by the company JM Huber Corporation and are sold under the Hubersorb® names. Methods for preparing these silicas are disclosed in greater detail in U.S. Pat. No. 4,557,916. Other suitable silicates are available from JM Huber Corporation, such as the sodium aluminosilicate sold under the Zeolexg brand name and the sodium magnesium aluminosilicate sold under the Hydrex® brand name.

Sebum-absorbing powders that may also be used include perlites, which are generally aluminosilicates of volcanic origin and which have the following composition:
70.0-75.0% by weight of silica $SiO_2$
12.0-15.0% by weight of aluminium oxide $Al_2O_3$
3.0-5.0% of sodium oxide $Na_2O$
3.0-5.0% of potassium oxide $K_2O$
0.5-2% of iron oxide $Fe_2O_3$
0.2-0.7% of magnesium oxide MgO
0.5-1.5% of calcium oxide CaO
0.05-0.15% of titanium oxide $TiO_2$.

Examples of zeolites that may especially be mentioned include sodium or potassium aluminosilicate compounds such as the product provided by Zeochem under the name Xmol.

The polylactic acids which can be used in the present invention are in particular Accurel EP600 from Akzo Nobel or the product provided under the name Lactic Acid Polymer 9105 by Dajac Labs.

Mention may be made, as silica powder, of:
the porous silica microspheres sold under the name Silica Beads SB-700 by the company Miyoshi; Sunsphere® H51 or Sunsphere® H33 by the company Asahi Glass;
the polydimethylsiloxane-coated amorphous silica microspheres sold under the name SA Sunsphere® H33 or SA Sunsphere® H53 by the company Asahi Glass.

Mention may be made, as nylon powder, of the nylon powder sold under the name Orgasol® 4000 by Atochem.

Mention may be made, as acrylic polymer powder, of:
the polymethyl methacrylate powders sold under the name Covabead® LH85 by the company Wackherr;
the polymethyl methacrylate/ethylene glycol dimethacrylate powders sold under the name Dow Corning 5640 Microsponge® Skin Oil Adsorber by the company Dow Corning; Ganzpearl® GMP-0820 by the company Ganz Chemical;
the poly(allyl methacrylate/ethylene glycol dimethacrylate) powders sold under the name Poly-Pore® L200 or Poly-Pore® E200 by Amcol Health and Beauty Solutions Inc.; these powders have in particular a sebum uptake of greater than or equal to 1 ml/g, better still ranging from 1 ml/g to 20 ml/g;
the ethylene glycol dimethacrylate/lauryl methacrylate copolymer powders sold under the name Polytrap® 6603 from the company Dow Corning.

Mention may be made, as silicone elastomer powder, of the powders sold under the names Trefil® Powder E-505C and Trefil® Powder E-506C by the company Dow Corning.

Preferably, the sebum-absorbing powder is chosen from modified starches such as starch octenylsuccinates and in particular aluminium starch octenylsuccinates, perlite, polylactic acids and zeolites, and better still from starch octenylsuccinates.

The sebum-absorbing powder(s) may be present in an amount preferably ranging from 0.1% to 99% by weight, even better still from 1% to 90% by weight and even more preferentially from 2% to 80% by weight, relative to the total weight of the composition.

The composition may also comprise one or more styling powders other than the sebum-absorbing powders.

The term "styling powder" means a powder consisting of one or more water-insoluble mineral compound(s) having a capacity for shaping the head of hair or for the durability of this shaping.

The water-insoluble mineral compound(s) is or are chosen from metal carbonates, oxides and sulfates, and silicates containing magnesium.

For the purposes of the present invention, the term "water-insoluble" means a compound of which the solubility at spontaneous pH in water at 25° C. and at atmospheric pressure is less than 0.1%.

Examples that may more particularly be mentioned include the carbonates, oxides and sulfates of alkaline-earth metals such as beryllium, magnesium, calcium, strontium, barium and radium, better still magnesium and calcium; the oxides, sulfates and carbonates of aluminium, gallium and indium; and silicates containing magnesium, particularly those containing an amount of magnesium of greater than 10% by weight (on a dry basis) as expressed in terms of magnesium oxide, such as Li—Mg—Na silicates, for instance Laponite XLG, which is provided by the company Rockwood.

More preferentially, use will be made of calcium carbonate, magnesium carbonate, alumina, barium sulfate and/or magnesium oxide, and even better still calcium carbonate. Preferably, these compounds have a mean particle size of from 20 to 50 μm, as water-insoluble mineral compound(s).

The water-insoluble mineral compound(s) may be present in an amount ranging from 0.1% to 99% by weight, even better still from 1% to 90% by weight and even more preferentially from 2% to 80% by weight, relative to the total weight of the composition.

According to the invention, the composition comprises one or more aluminium salt(s) other than the sebum-absorbing powders with a sebum uptake of greater than or equal to 35 ml/100 g, and/or than the styling powders.

The aluminium salts according to the invention may be of organic or mineral nature.

Preferably, the aluminium salts according to the invention are mineral salts.

The aluminium salts in accordance with the invention are preferably chosen from the aluminium halohydrates, in particular aluminium chlorohydrates; aluminium zirconium halohydrates; and complexes of zirconium hydroxychloride and of aluminium hydroxychloride with an amino acid, such as those described in U.S. Pat. No. 3,792,068, commonly known as "ZAG complexes".

Among the aluminium salts, mention may in particular be made of aluminium chlorohydrate in activated or unactivated form, aluminium chlorohydrex, the aluminium chlorohydrex-polyethylene glycol complex, the aluminium chlorohydrex-propylene glycol complex, aluminium dichlorohydrate, the aluminium dichlorohydrex-polyethylene glycol complex, the aluminium dichlorohydrex-propylene glycol complex, aluminium sesquichlorohydrate, the aluminium sesquichlorohydrex-polyethylene glycol complex, the aluminium sesquichlorohydrex-propylene glycol complex, aluminium sulfate buffered with sodium aluminium lactate, and potassium aluminium sulfates, in particular alum. Mention will be made, for example, of the aluminium potassium sulfate dodecahydrates sold by the company Soliance under the name Silkalun.

Among the aluminium zirconium salts, mention may be made in particular of aluminium zirconium octachlorohydrate, aluminium zirconium pentachlorohydrate, aluminium zirconium tetrachlorohydrate and aluminium zirconium trichlorohydrate. Aluminium zirconium salts are, for example, the salt sold by the company Reheis under the name Reach AZP-908-SUF.

The complexes of zirconium hydroxychloride and of aluminium hydroxychloride with an amino acid are generally known as ZAG (when the amino acid is glycine). Among these products, mention may be made of the aluminium zirconium octachlorohydrex-glycine complexes, the aluminium zirconium pentachlorohydrex-glycine complexes, the aluminium zirconium tetrachlorohydrex-glycine complexes and the aluminium zirconium trichlorohydrex-glycine complexes.

The aluminium salts which may be used according to the invention may be in hydrated form.

Preferably, the aluminium salts are chosen from optionally hydrated potassium aluminium sulfates, aluminium halohydrates, in particular aluminium chlorohydrates, more preferably still from optionally hydrated potassium aluminium sulfates, in particular alum.

The aluminium salt(s) may be present in an amount ranging from 0.01% to 15% by weight, even better still from 0.05% to 10% by weight and even more preferentially from 0.1% to 5% by weight, relative to the total weight of the composition.

According to one particular embodiment, the composition according to the invention may also comprise one or more zinc salts.

The zinc salts may be of organic or mineral nature, preferably of organic nature. The organic zinc salt may be chosen especially from zinc gluconate, zinc lactate, zinc glycinate, zinc aspartate, zinc pyrrolidonecarboxylate (more commonly known as zinc pidolate), zinc phenolsulfonate, zinc salicylate, zinc citrate, zinc acetate, zinc ricinoleate, zinc pyrithione and mixtures thereof.

Preferably, the zinc salt is chosen from zinc gluconate, zinc salicylate, zinc ricinoleate, zinc pyrithione and zinc pidolate, and more preferably still is zinc pidolate.

When they are present, the zinc salts are present in an amount ranging from 0.01% to 15% by weight, preferably from 0.05% to 10% by weight and even more preferentially from 0.1% to 5% by weight, relative to the total weight of the composition.

As indicated previously, the composition according to the invention may also contain one or more propellants.

The propellant which may be used in the composition according to the invention may be chosen from air, nitrogen, carbon dioxide, dimethyl ether, volatile hydrocarbons such as, in particular, $C_3$-$C_5$ alkanes, chlorinated and/or fluorinated hydrocarbons such as 1,1-difluoroethane and mixtures thereof, preferably chosen from $C_3$-$C_3$ alkanes and preferably n-butane, propane, isobutane and mixtures thereof.

Mention may be made preferentially of $C_3$-$C_3$ alkanes and in particular propane n-butane and isobutane and mixtures thereof.

When they are present in the composition, the propellant(s) is or are present in an amount ranging from 10% to 95% by weight, even better still from 15% to 90% by weight and even more preferentially from 20% to 88% by weight, relative to the total weight of the composition.

The composition of the invention may also comprise one or more liquid fatty substances.

The term "fatty substance" means an organic compound that is insoluble in water at standard temperature (25° C.) and at atmospheric pressure (760 mmHg, i.e. $1.013 \times 10^5$ Pa), i.e. with a solubility of less than 5%, preferably of less than 1% and even more preferentially of less than 0.1%.

The fatty substances are preferably non-siliceous, that is to say their structure does not contain a silicon atom. They generally have in their structure a hydrocarbon-based chain comprising at least 6 carbon atoms and not comprising any siloxane group.

In addition, the fatty substances are generally soluble in organic solvents under the same temperature and pressure conditions, for instance chloroform, ethanol, benzene, liquid petroleum jelly or decamethylcyclopentasiloxane.

The liquid fatty substances that may be used in the invention are liquid at ambient temperature (25° C.) and under atmospheric pressure (760 mmHg, i.e. $1.013 \times 10^5$ Pa). They preferably have a viscosity of less than or equal to 2 Pa·s, better still less than or equal to 1 Pa·s, and even better still less than or equal to 0.1 Pa·s at a temperature of 25° C. and at a shear rate of 1 $s^{-1}$.

The liquid fatty substances that may be used in the composition according to the invention are generally not oxyalkylenated and preferably do not contain any carboxylic acid COOH functions.

The liquid fatty substances are preferably chosen from hydrocarbons, fatty alcohols, fatty esters and fatty ethers, and mixtures thereof.

Even more preferentially, they are chosen from hydrocarbons, fatty alcohols and fatty esters, and mixtures thereof.

The term "liquid hydrocarbon" means a hydrocarbon composed solely of carbon and hydrogen atoms, which is liquid at standard temperature (25° C.) and at atmospheric pressure (760 mmHg, i.e. $1.013 \times 10^5$ Pa), which is especially of mineral or plant or synthetic origin.

More particularly, the liquid hydrocarbons are chosen from:
linear or branched, optionally cyclic, $C_6$-$C_{16}$ alkanes. Examples that may be mentioned include hexane, undecane, dodecane, tridecane, and isoparaffins, for instance isohexadecane, isododecane and isodecane,
linear or branched hydrocarbons of mineral, animal or synthetic origin with more than 16 carbon atoms, such as liquid paraffin or liquid petroleum jelly, polydecenes, hydrogenated polyisobutene such as the product sold under the brand name Parleam® by the company NOF Corporation, and squalane.

In one preferred variant, the liquid hydrocarbon(s) is or are chosen from liquid paraffin and liquid petroleum jelly.

The term "liquid fatty alcohol" means a non-glycerolated and non-oxyalkylenated fatty alcohol which is liquid at standard temperature (25° C.) and at atmospheric pressure (760 mmHg; i.e. $1.013 \times 10^5$ Pa).

Preferably, the liquid fatty alcohols of the invention comprise from 8 to 30 carbon atoms.

The liquid fatty alcohols of the invention may be saturated or unsaturated.

The saturated liquid fatty alcohols are preferably branched. They may optionally comprise in their structure at least one aromatic or non-aromatic ring. They are preferably acyclic.

More particularly, the liquid saturated fatty alcohols of the invention are chosen from octyldodecanol, isostearyl alcohol and 2-hexyldecanol.

Octyldodecanol is most particularly preferred.

The unsaturated liquid fatty alcohols contain in their structure at least one double or triple bond, and preferably one or more double bonds. When several double bonds are present, there are preferably 2 or 3 of them, and they may be conjugated or unconjugated.

These unsaturated fatty alcohols may be linear or branched.

They may optionally comprise in their structure at least one aromatic or non-aromatic ring. They are preferably acyclic.

More particularly, the unsaturated liquid fatty alcohols of the invention are chosen from oleyl alcohol, linoleyl alcohol, linolenyl alcohol and undecylenyl alcohol.

Oleyl alcohol is most particularly preferred.

The term "liquid fatty ester" means an ester derived from a fatty acid and/or from a fatty alcohol, that is liquid at standard temperature (25° C.) and at atmospheric pressure (760 mmHg, i.e. $1.013 \times 10^5$ Pa).

The esters are preferably liquid esters of saturated or unsaturated, linear or branched, $C_1$-$C_{26}$ aliphatic monoacids or polyacids and of saturated or unsaturated, linear or branched, $C_1$-$C_{26}$ aliphatic monoalcohols or polyalcohols, the total number of carbon atoms in the esters being greater than or equal to 10.

Preferably, for the esters of monoalcohols, at least one of the alcohol or of the acid from which the esters of the invention result is branched.

Among the monoesters of monoacids and of monoalcohols, mention may be made of ethyl isopropyl palmitates, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of mono-, di- or tricarboxylic acids and of $C_4$-$C_{26}$ non-sugar di-, tri-, tetra- or pentahydroxylated alcohols may also be used.

Mention may be made especially of diethyl sebacate, diisopropyl sebacate, bis(2-ethylhexyl) sebacate, diisopropyl adipate, di-n-propyl adipate, dioctyl adipate, bis(2-ethylhexyl) adipate, diisostearyl adipate, bis(2-ethylhexyl) maleate, triisopropyl citrate, triisocetyl citrate, triisostearyl citrate, glyceryl trilactate, glyceryl trioctanoate, trioctyldodecyl citrate, trioleyl citrate, neopentyl glycol diheptanoate, and diethylene glycol diisononanoate.

The composition may further comprise, as liquid fatty ester, sugar esters and diesters of $O_6$-$O_{30}$ fatty acids, preferably $C_{12}$—$O_{22}$ fatty acids. It is recalled that the term "sugar" means oxygen-bearing hydrocarbon-based compounds which contain a plurality of alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose, glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, and polyesters, and mixtures thereof.

These esters may be, for example, oleates, laurates, palmitates, myristates, behenates, cocoates, stearates, linoleates, linolenates, caprates or arachidonates, or mixtures thereof, such as, especially, oleopalmitate, oleostearate or palmitostearate mixed esters.

More particularly, use is made of monoesters and diesters and especially of sucrose, glucose or methylglucose mono- or dioleates, stearates, behenates, oleopalmitates, linoleates, linolenates or oleostearates.

An example that may be mentioned is the product sold under the name Glucate® DO by the company Amerchol, which is a methylglucose dioleate.

Finally, use may also be made of natural or synthetic glycerol esters of mono-, di- or triacids.

Among these, mention may be made of plant oils.

As oils of plant origin or synthetic triglycerides that may be used in the composition of the invention as liquid fatty esters, examples that may be mentioned include:

triglyceride oils of plant or synthetic origin, such as liquid fatty acid triglycerides containing from 6 to 30 carbon atoms, for instance heptanoic or octanoic acid triglycerides, or alternatively, for example, sunflower oil, maize oil, soya bean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, safflower oil, candlenut oil, camelina oil, tamanu oil, babassu oil and pracaxi oil, caprylic/capric acid triglycerides, for instance those sold by the company Stéarineries Dubois or those sold under the names Miglyol® 810, 812 and 818 by the company Dynamit Nobel, jojoba oil and shea butter oil.

Liquid fatty esters derived from monoalcohols will preferably be used as esters according to the invention.

Isopropyl myristate or isopropyl palmitate are particularly preferred.

The liquid fatty ethers are chosen from liquid dialkyl ethers such as dicaprylyl ether.

Preferably, the liquid fatty substances are chosen from linear or branched hydrocarbons of mineral, animal or synthetic origin and with more than 16 carbon atoms, branched or unsaturated fatty alcohols, fatty esters and triglyceride oils of plant origin.

More preferentially, the liquid fatty substances are chosen from liquid paraffin or liquid petroleum jelly, octyldodecanol, isostearyl alcohol, 2-hexyldecanol, oleyl alcohol, linoleyl alcohol, linolenyl alcohol and undecylenyl alcohol, ethyl and isopropyl palmitates, alkyl myristates such as isopropyl myristate or ethyl myristate, isocetyl stearate, 2-ethylhexyl isononanoate, isononyl isononanoate, isodecyl neopentanoate and isostearyl neopentanoate, and plant oils.

Even more preferentially, the liquid fatty substances are chosen from isopropyl palmitate and isopropyl myristate.

When they are present, the liquid fatty substance(s) is or are present in an amount ranging preferably from, for example, 0.05% to 20% by weight, better still from 0.1% to 10% by weight and even better still from 0.2% to 5% by weight, relative to the total weight of the composition.

The composition according to the invention may also contain one or more additives chosen from conditioning or fixing anionic, cationic, nonionic, amphoteric or zwitterionic polymers, fragrances, dyes, protective screening agents, acids, bases, nacres and glitter flakes.

These additives may be present in the composition according to the invention in an amount ranging from 0 to 20% by weight relative to the total weight of the composition.

A person skilled in the art will take care to choose these optional additives and their amounts so that they do not harm the properties of the compositions of the present invention.

According to one embodiment, the compositions in powder form in accordance with the invention may be packaged in a container comprising one or more dispensing orifices, of the salt shaker type.

According to another embodiment, the compositions in powder form in accordance with the invention may be packaged in an aerosol device composed of a container comprising the composition and a means for dispensing the said composition.

According to this embodiment, the container is pressurized. The container may be opaque or transparent. It can be made of glass, of polymer or of metal, optionally covered with a protective lacquer layer.

The container may therefore contain both the propellant(s) and the other ingredients of the composition, in a single compartment, or as a variant in two compartments. According to the latter variant, the container may consist of an outer aerosol can comprising an inner bag hermetically welded to a valve. The various ingredients of the composition are introduced into the inner bag and a propellant is introduced between the bag and the can at a sufficient pressure to make the product come out in the form of a spray.

The container is equipped at its top end with a valve that seals the system.

For example, it is possible to use a valve sold by the companies Precision, Coster, Seaquist and Lindal.

The device, packaged with such a valve, ensures the sealing of the system, and also the dispensing of the product from the container.

The present invention also relates to a process for the dry-washing and cosmetic treatment of the hair, comprising the application to the hair, preferably dry hair, of a composition as described above.

The present invention also relates to the use of the composition defined above for the dry-washing and cosmetic treatment of the hair.

EXAMPLE

In the example that follows, all the amounts are indicated as weight percentages of product in unmodified form relative to the total weight of the composition.

The following compositions according to the invention may be produced starting from the compounds indicated in the table below, composition A being able to be packaged in an aerosol device and composition B in a salt-shaker-type device:

|  | A | B |
| --- | --- | --- |
| DRY FLO PLUS by National Starch (86% Aluminium Starch Octenylsuccinate) | 10.42 | 74.00 |
| Calcium carbonate (D50 = 35 µm)[1] | 2.18 | 15.00 |
| Hectorite modified with distearyldimethylammonium chloride[2] | 0.28 | 2.00 |
| Isopropyl myristate | 0.42 | 3.00 |
| Fragrance | 0.20 | 1.00 |

-continued

|  | A | B |
|---|---|---|
| Hydrated potassium aluminium sulfate (alum $KAl(SO_4)_2 \cdot 12H_2O$) | 0.50 | 5.00 |
| Isobutane | 86.00 | — |

[1] Sold under the trade name Omyacare S60 by Omya
[2] Sold under the trade name Bentone 38 by Elementis The following compositions according to the invention C, D and E, and comparative compositions F and G, were prepared from the compounds indicated in the table below.

|  | C | D | E | F | G |
|---|---|---|---|---|---|
| DRY FLO PLUS by National Starch (86% Aluminium Starch Octenylsuccinate) | 12.41 | 89.00 | 11.92 | 12.90 | 10.92 |
| Calcium carbonate (D50 = 35 μm)[1] | 0.20 | 1.50 | 0.20 | 0.20 | 2.18 |
| Hectorite modified with distearyldimethylammonium chloride[2] | 0.28 | 2.00 | 0.28 | 0.28 | 0.28 |
| Isopropyl myristate | 0.42 | 3.00 | 0.42 | 0.42 | 0.42 |
| Fragrance | 0.20 | 1.00 | 0.20 | 0.20 | 0.20 |
| Hydrated potassium aluminium sulfate (alum $KAl(SO_4)_2 \cdot 12H_2O$) | 0.49 | 3.50 | 0.49 | — | — |
| Zinc pidolate | — | — | 0.49 | — | — |
| Isobutane | 86.00 | — | 86.00 | 86.00 | 86.00 |

[1] Sold under the trade name Omyacare S60 by Omya
[2] Sold under the trade name Bentone 38 by Elementis Assessment of Cleansing and/or Anti-Grease Power of the Composition Compositions C, E, F and G were introduced in powder form, without the isobutane, into an aerosol device. The isobutane was then introduced to pressurize the device. The device is fitted with a valve conventionally used for aerosols.

Composition D was introduced in powder form into a salt-shaker-type container.

Compositions C, D, E and G were applied to 2.7 g of natural locks according to the following protocol:

Each lock was combed and tared beforehand on aluminium foil. 0.1 g of artificial sebum was applied, and spread by finger along the lock.

Each lock was then combed with one passage of a comb.

4 g of composition were then applied to the lock with its aluminium foil. In particular, compositions C and E according to the invention and comparative composition G were sprayed and composition D was deposited by gravity.

The composition was spread by finger along the lock with 10 circular motions.

Each lock was then combed with one passage of a comb.

Six experts assessed the following criteria:
the visual appearance—greasy or clean;
the feel—greasy or natural;
the appearance of the hair—in clumps or individual strands;
the appearance of the hair—fixed in place or supple;
the appearance of the hair—flattened or instead with volume.

All the experts judged the visual appearance of the locks treated with the compositions of the invention to be cleaner, with a more natural feel and more individualised strands of hair and to be more supple with more volume compared to the locks treated with composition G.

Assessment of the Stability of the Composition

Sedimentation test: Compositions C and F were also packaged in aerosol form in a transparent glass container with 100 ml capacity (dimensions: 4 cm diameter and 13 cm height). The container was filled with 33 g of composition. The container was shaken vigorously. Then, the sedimentation rate was noted visually by timing the sedimentation of the suspension at rest until sedimentation at 1 cm from the upper level of the composition and until complete sedimentation.

Protocol:
$t_0$: starting the timer.
$t_1$: time to partial sedimentation, i.e. at 1 cm from the upper level of the composition.
$t_{final}$: time to total sedimentation, i.e. until the clear and stable supernatant is obtained.

The results are averaged over 3 measurements.

|  | Composition C | Composition F |
|---|---|---|
| $t_1$ | 7 seconds | 5 seconds |
| $t_{final}$ | 38 seconds | 25 seconds |

Composition C of the invention takes more time to sediment than composition F and is therefore more stable.

It is thus noted that the addition of alum allows the sedimentation time to be increased compared to that of a composition without alum.

The invention claimed is:

1. A method for dry-washing hair on the scalp, said method comprising applying to the hair on the scalp a composition comprising:
   a) at least one sebum-absorbing powder with a sebum uptake of greater than or equal to about 35 mL/100 g;
   b) at least one aluminum salt other than the sebum-absorbing powder, wherein the aluminum salt is chosen from optionally hydrated potassium aluminum sulfates or aluminum halohydrates;
   c) optionally, at least one propellant; and
   d) at least one styling powder.

2. The method according to claim 1, wherein the at least one sebum-absorbing powder is chosen from modified starches.

3. The method according to claim 1, wherein the at least one sebum-absorbing powder is chosen from starch octenylsuccinates, aluminum starch octenylsuccinates, perlite, polylactic acids, or zeolites.

4. The method according to claim 1, wherein the at least one sebum-absorbing powder is present in an amount ranging from about 0.1% to about 99% by weight, relative to the total weight of the composition.

5. The method according to claim 1, wherein the at least one sebum-absorbing powder is present in an amount ranging from about 2% to about 80% by weight, relative to the total weight of the composition.

6. The method according to claim 1, wherein the at least one styling powder comprises at least one water-insoluble mineral compound.

7. The method according to claim 6, wherein the at least one water-insoluble mineral compound is chosen from metal carbonates, oxides, sulfates, or silicates containing magnesium.

8. The method according to claim 6, wherein the at least one water-insoluble mineral compound is chosen from calcium carbonate, magnesium carbonate, alumina, barium sulfate, or magnesium oxide.

9. The method according to claim 6, wherein the at least one water-insoluble mineral compound is present in an amount ranging from about 0.1% to about 99% by weight, relative to the total weight of the composition.

10. The method according to claim 6, wherein the at least one water-insoluble mineral compound is present in an amount ranging from about 2% to about 80% by weight, relative to the total weight of the composition.

11. The method according to claim 1, wherein the at least one aluminum salt is present in an amount ranging from about 0.01% to about 15% by weight, relative to the total weight of the composition.

12. The method according to claim 1, wherein the at least one aluminum salt is present in an amount ranging from about 0.1% to about 5% by weight, relative to the total weight of the composition.

13. The method according to claim 1, wherein the composition is anhydrous.

14. The method according to claim 1, further comprising at least one zinc salt chosen from zinc gluconate, zinc salicylate, zinc ricinoleate, zinc pyrithione, or zinc pidolate.

15. The method according to claim 1, wherein the at least one propellant is chosen from air, nitrogen, carbon dioxide, dimethyl ether, volatile hydrocarbons, chlorinated and/or fluorinated hydrocarbons, or mixtures thereof.

16. The method according to claim 1, wherein the at least one propellant is chosen from $C_3$-$C_5$ alkanes.

17. The method according to claim 1, wherein the at least one propellant is chosen from n-butane, propane, isobutane, or mixtures thereof.

18. The method according to claim 1, wherein the at least one propellant is present in an amount ranging from about 10% to about 95% by weight, relative to the total weight of the composition.

19. The method according to claim 1, wherein the at least one propellant is present in an amount ranging from about 20% to about 88% by weight, relative to the total weight of the composition.

20. The method according to claim 1, further comprising at least one liquid fatty substance.

21. The method according to claim 20, wherein the at least one liquid fatty substance is chosen from linear or branched hydrocarbons of mineral, animal or synthetic origin and with more than 16 carbon atoms, branched or unsaturated fatty alcohols, fatty esters, or triglyceride oils of plant origin.

22. The method according to claim 20, wherein the at least one liquid fatty substance is chosen from liquid paraffin, liquid petroleum jelly, octyldodecanol, isostearyl alcohol, 2-hexyldecanol, oleyl alcohol, linoleyl alcohol, linolenyl alcohol or undecylenyl alcohol, ethyl or isopropyl palmitates, alkyl myristates, isocetyl stearate, 2-ethylhexyl isononanoate, isononyl isononanoate, isodecyl neopentanoate, isostearyl neopentanoate, or plant oils.

23. The method according to claim 20, wherein the at least one liquid fatty substance is chosen from isopropyl palmitate or isopropyl myristate.

\* \* \* \* \*

UNITED STATES PATENT AND TRADEMARK OFFICE
CERTIFICATE OF CORRECTION

PATENT NO.        : 10,449,140 B2
APPLICATION NO.   : 15/523242
DATED             : October 22, 2019
INVENTOR(S)       : Lionel Aubert et al.

It is certified that error appears in the above-identified patent and that said Letters Patent is hereby corrected as shown below:

On the Title Page

Item (57), Line 8, please change "thy-washing" to -- dry-washing --.

Signed and Sealed this
Third Day of December, 2019

Andrei Iancu
*Director of the United States Patent and Trademark Office*